(12) United States Patent
Kane

(10) Patent No.: US 6,358,730 B1
(45) Date of Patent: Mar. 19, 2002

(54) FILTRATION ASSEMBLY AND CULTURE DEVICE

(75) Inventor: Jeffrey Kane, Manchester, MI (US)

(73) Assignee: Pall Corporation, East Hills, NY (US)

( * ) Notice: Subject to any disclaimer, the term of this patent is extended or adjusted under 35 U.S.C. 154(b) by 0 days.

(21) Appl. No.: 09/355,423

(22) PCT Filed: Jan. 28, 1998

(86) PCT No.: PCT/US98/01594

§ 371 Date: Jul. 26, 1999

§ 102(e) Date: Jul. 26, 1999

(87) PCT Pub. No.: WO98/32875

PCT Pub. Date: Jul. 30, 1998

Related U.S. Application Data

(60) Provisional application No. 60/036,310, filed on Jan. 29, 1997.

(51) Int. Cl.$^7$ .............................. C12M 1/12; C12M 1/22
(52) U.S. Cl. ................................ 435/297.5; 435/287.1; 435/288.3; 435/30; 435/401; 422/101
(58) Field of Search ............................. 435/30, 34, 39, 435/401, 287.1, 287.7, 287.9, 288.3, 297.2, 297.5, 305.1, 305.4, 308.1; 422/101; 210/406, 416.1, 767

(56) References Cited

U.S. PATENT DOCUMENTS

| | | |
|---|---|---|
| 2,904,857 A | 9/1959 | Goetz .............................. 21/82 |
| 2,923,669 A | 2/1960 | Poitras ..................... 195/103.5 |

(List continued on next page.)

FOREIGN PATENT DOCUMENTS

GB 1351752 5/1974

OTHER PUBLICATIONS

"145, 147 Analytical Test Filter Funnels", Products catalog of Nalge Nunc International from nalgenelab.nalgenunc-.com on Jul. 28, 1999.

Primary Examiner—William H. Beisner
(74) Attorney, Agent, or Firm—Leydig, Voit & Mayer, Ltd.

(57) ABSTRACT

A filtration assembly can comprise a chamber for holding a fluid sample to be filtered and a cover assembly defining a petri dish into which a filter element can be placed for cultivating microorganisms present on the filter element. A filtration assembly can also comprise a sample reservoir for holding a fluid sample and a base for supporting the sample reservoir detachably connected to the sample reservoir. One of the sample reservoir and the base can have a projection extending around its periphery and the other of the sample reservoir and the base can have a groove extending around its periphery and detachably engaging the projection in a fluid-type manner around its periphery. A filtration assembly can also comprise a sample reservoir for holding a fluid sample to be filtered and a base for supporting the sample reservoir. The base can include a fluid port and communication with an interior of the sample reservoir and a skirt surrounding the fluid port for contact with a vacuum manifold. A method of filtering a fluid may comprise disposing a filter element on a support surface formed on one of a sample reservoir and a base. The method can further comprise detachably connecting the sample reservoir to the base in a fluid type manner without using the ceiling member by engagement between a projection formed on one of the sample reservoir and the base and a groove formed in the other of the sample reservoir and the base. A method of using a filtration assembly can comprise placing a base of a filtration assembly on a vacuum manifold with a skirt of the base contacting an inlet tube of the manifold around the periphery of the skirt. A method of culturing microorganisms can comprise passing the fluid sample through a filter element and placing the filter element in a petri dish defined by a cover assembly mountable on a sample reservoir.

21 Claims, 14 Drawing Sheets

U.S. PATENT DOCUMENTS

| | | |
|---|---|---|
| 3,295,686 A | 1/1967 | Krueger ..................... 210/455 |
| 3,448,011 A | 6/1969 | Russomanno ............... 195/139 |
| 3,684,660 A | 8/1972 | Kereluk et al. ............. 195/139 |
| 4,111,807 A | 9/1978 | Boomus et al. ............. 210/152 |
| 4,148,732 A | 4/1979 | Burrow et al. .............. 210/232 |
| 4,170,056 A | 10/1979 | Meyst et al. ............... 29/163.5 |
| 4,251,366 A | 2/1981 | Simon et al. ............... 210/767 |
| 4,357,240 A | 11/1982 | Mehra et al. ............... 210/455 |
| 4,614,585 A | 9/1986 | Mehra et al. ............ 210/433.2 |
| 4,678,576 A | 7/1987 | Leoncavallo ............. 210/433.2 |
| 4,689,147 A | 8/1987 | Leoncavallo et al. ........ 210/232 |
| 4,826,594 A | 5/1989 | Sedman ..................... 210/266 |
| 4,829,005 A | 5/1989 | Friedman et al. ........... 435/296 |
| 5,112,488 A | 5/1992 | Lemonnier .................. 210/541 |
| 5,141,639 A | 8/1992 | Kraus et al. ........... 210/321.75 |
| 5,200,067 A | 4/1993 | Sann .......................... 210/172 |
| 5,202,262 A | 4/1993 | Lemonnier .................. 435/299 |
| 5,234,585 A | 8/1993 | Zuk, Jr. ...................... 210/188 |
| 5,308,483 A | 5/1994 | Sklar et al. ................. 210/232 |

FILTRATION ASSEMBLY AND CULTURE DEVICE

This application claims the benefit of U.S. Provisional Application No. 60/036,310 filed Jan. 29, 1997.

BACKGROUND OF THE INVENTION

1. Field of the Invention

This invention relates to a filtration assembly which can be used for culturing microorganisms.

2. Description of the Related Art

A common method of investigating for the presence of microorganisms in a fluid is to pass the fluid through a filter element capable of capturing microorganisms larger than a certain size present in the fluid. After the completion of filtration, the filter element and any microorganisms captured by it are placed in a petri dish containing a nutrient solution. The nutrient solution permeates through the filter element to reach the microorganisms, enabling the microorganisms to be cultured atop the filter element.

The filtration of the fluid containing the microorganisms is typically performed using a filtration assembly including a fluid reservoir connected to a base on which a filter element can be removably disposed. A petri dish for receiving the filter element after filtration forms no part of the filtration assembly, so a separate petri dish is required in order for culturing of microorganisms to take place.

SUMMARY OF THE INVENTION

The present invention provides a filtration assembly which can be used both for filtering a fluid containing microorganisms and for culturing microorganisms removed from the fluid by the filtration.

The present invention also provides a method of culturing microorganisms.

According to one form of the present invention, a filtration assembly includes a chamber for holding a fluid sample to be filtered, a fluid port for filtrate in fluid communication with the chamber, a filter support arranged to support a filter element on a flow path between the chamber and the fluid port, and a cover assembly including a lower cover detachably mounted on the chamber and an upper cover detachably mounted on the lower cover. The cover assembly defines a petri dish into which a filter element can be placed for cultivating microorganisms present on the filter element. The ability of the cover assembly to be used as a petri dish makes the filtration assembly highly convenient to use and renders a separate petri dish unnecessary.

In one preferred embodiment, the assembly includes a sample reservoir which defines the chamber, and a base which includes a fluid port and the support surface. The sample reservoir and the base may be permanently connected to each other, or they may be detachable from each other to permit the base to be used separately from the sample reservoir with one of the covers as a petri dish.

In some embodiments, the filtration assembly includes a sample reservoir for holding a fluid sample, and a base for supporting the sample reservoir. The base may be detachably connected to the sample reservoir in a fluid-tight manner without use of a sealing member between the sample reservoir and the base. Because no sealing member is required between the sample and the base, the manufacturing costs of the filtration assembly can be reduced.

In some embodiments, the filtration assembly includes a sample reservoir for holding a fluid sample to be filtered and a base for supporting the sample reservoir. The base includes a fluid port and a skirt surrounding the fluid port for contact with a vacuum manifold of a vacuum filtration assembly. The skirt makes it unnecessary to provide a stopper or an adapter for connecting the base to a vacuum manifold, so the filtration assembly is easy to use.

According to another form of the present invention, a method of culturing microorganisms comprises introducing a fluid sample into a sample reservoir, passing the fluid sample through a filter element communicating with an interior of the sample reservoir to filter the fluid; after filtering the fluid, placing the filter element in a petri dish defined by a cover assembly mountable on the sample reservoir and comprising first and second covers; and incubating microorganisms in the petri dish.

In some embodiments, the method includes disposing a filter element on a filter support surface of a sample reservoir or a base, detachably connecting the sample reservoir to the base in a fluid-tight manner without using a sealing member, introducing a fluid sample into the sample reservoir, and removing fluid which has passed through the filter element from a fluid port of the base.

In some embodiments, the method includes placing a base of a filtration assembly on a vacuum manifold with a skirt of the base contacting an inlet tube of the manifold, and applying suction to an interior of the inlet tube to draw a fluid through a filter element within the filtration assembly and into the manifold.

These and other various aspects of the present invention will be explained in farther detail by the following description and the accompanying drawings.

DESCRIPTION OF PREFERRED EMBODIMENTS

Figure 1:
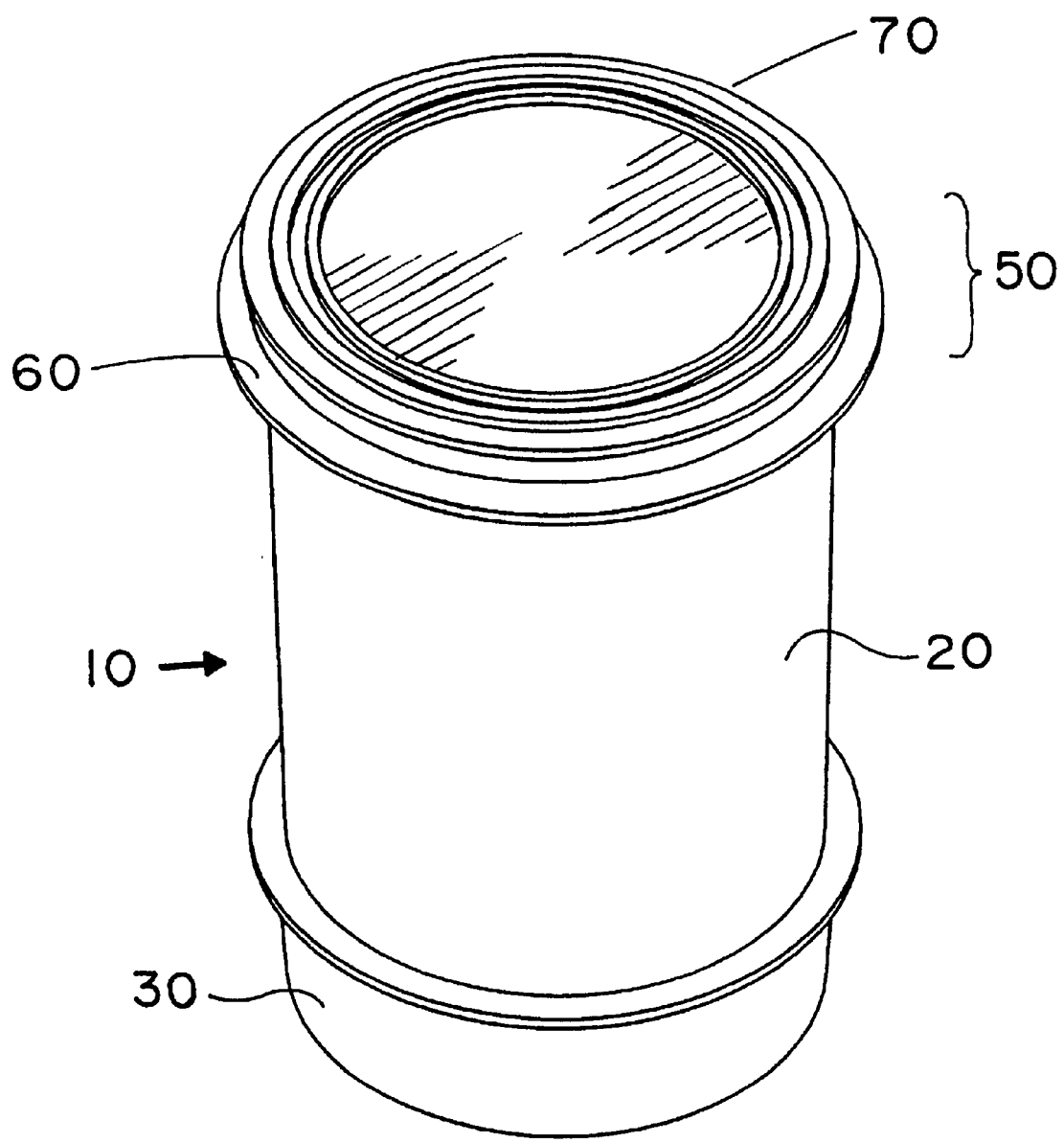
FIG. 1 is an isometric view of an embodiment of a filtration assembly according to the present invention.

FIGS. 1–8 illustrate an embodiment of a filtration assembly 10 according to the present invention. As shown in these figures, the assembly 10 includes a sample reservoir 20, a base 30 which is detachably engageable with the lower end of the sample reservoir 20, and a cover assembly 50 which is detachably mounted atop the sample reservoir 20. The sample reservoir 20 defines a chamber 22 which can hold a fluid sample which is to be filtered, while the base 30 serves to support the sample reservoir 20 as well as a filter element 45 through which the fluid sample is to be passed. In the present embodiment, the cover assembly 50 is designed to function as a petri dish by itself, or a portion of the cover assembly 50 may be combined with the base 30 to form a petri dish.

The sample reservoir 20 may have any structure which enables it to hold a desired volume of a sample fluid which is to be filtered. In the present embodiment, the sample reservoir 20 is a generally cylindrical member, i.e., a body of revolution, which is open at its upper and lower ends. It has an outer wall 21 which defines the outer periphery of the chamber 22 for the sample fluid. The outer wall 21 has a circular transverse cross-sectional shape and an inner diameter which linearly decreases from its upper to its lower end, but the shape of the outer wall 21 is not critical, and its diameter need not vary over its height. For example, the transverse cross-sectional shape may be polygonal or of a non-circular curved shape, and the inner diameter or other dimensions of the sample reservoir 20 may be constant or vary in any desired manner over the height of the sample reservoir 20. The sample reservoir 20 may be equipped with gradations on its inner or outer surface to assist a user in measuring the amount of sample fluid being introduced into the sample reservoir 20.

Figure 4:
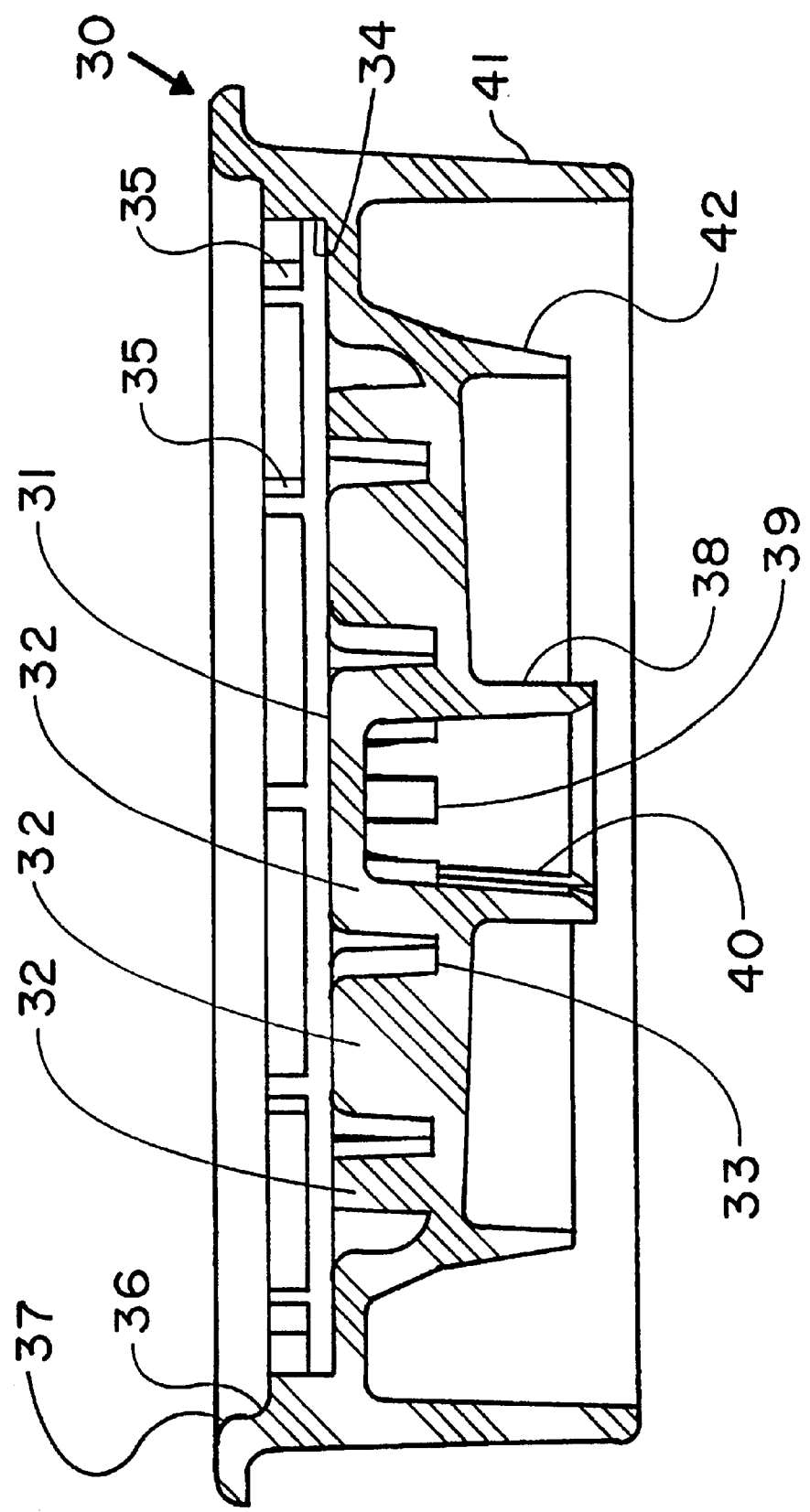
FIG. 4 is a vertical cross-sectional view of the base of the embodiment of FIG. 1.
Figure 5:
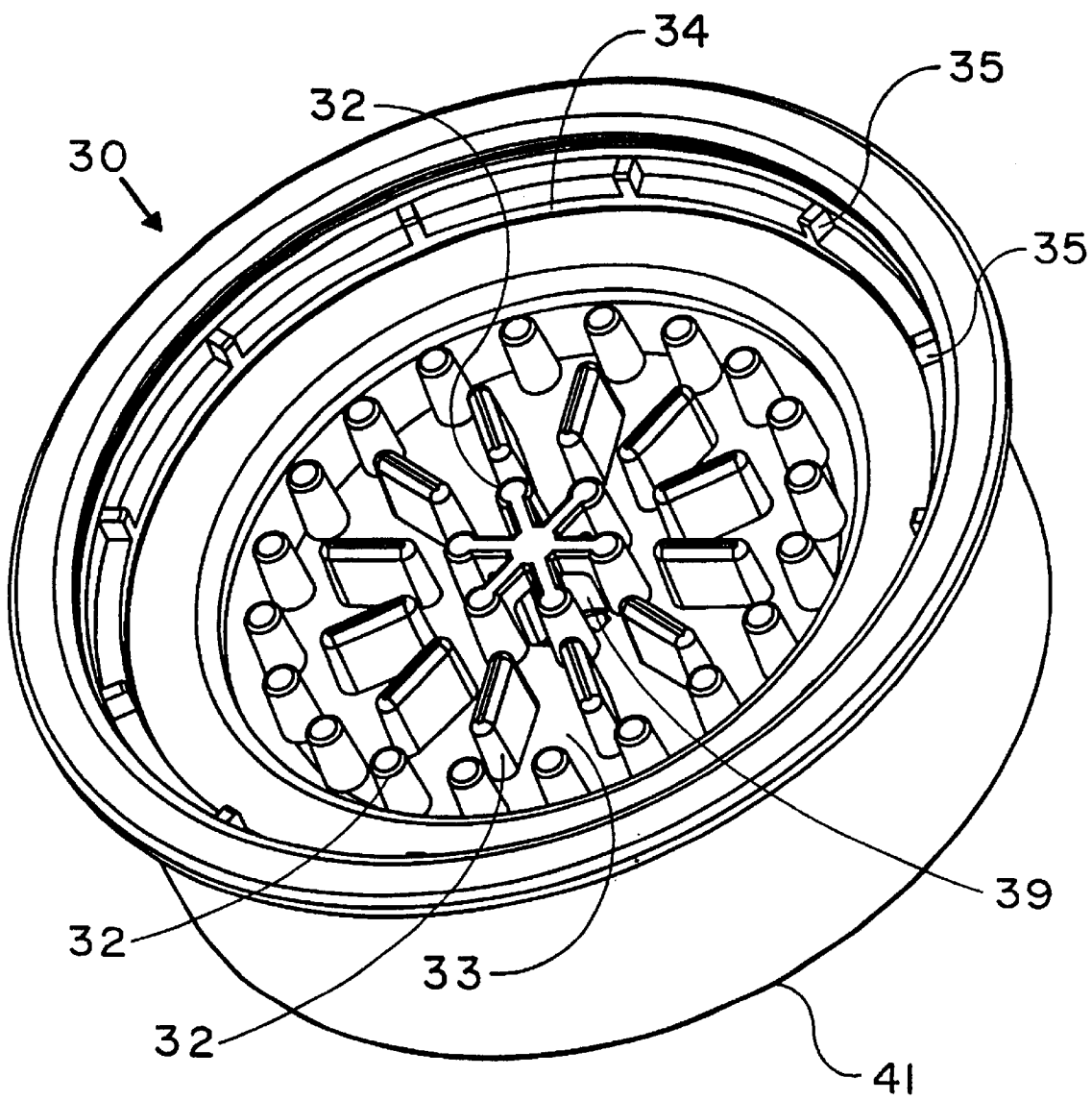
FIG. 5 is a top isometric view of the base.
Figure 6:
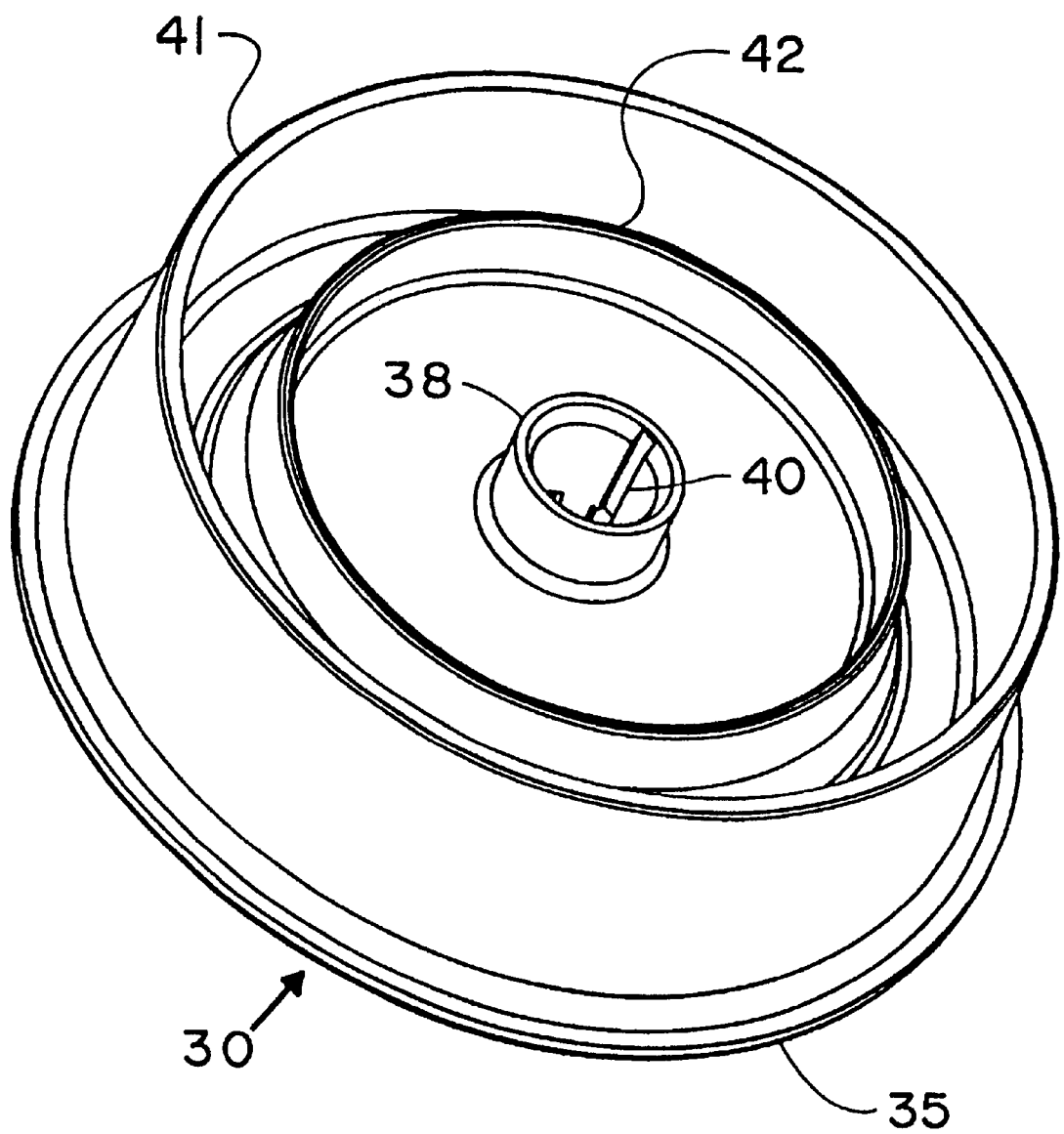
FIG. 6 is a bottom isometric view of the base.

As best shown in FIGS. 4 and 5, which are respectively a vertical cross-sectional view and a top isometric view of the base 30, the base 30 includes a filter support surface 31 atop which a filter element 45 can be supported during filtration and a fluid port 38 through which filtrate which has passed through the filter element 45 can be discharged from the filtration assembly 10. The filter support surface 31 is defined by the upper surfaces of a plurality of projections 32 which extend upwards from a bottom inner surface 33 of the base 30. The projections 32 are spaced from each other to enable filtrate which has passed through the filter element 45 to flow between the projections 32 into the fluid port 38. One or more drainage openings 39 for filtrate are formed in the projections 32 at the center of the base 30 to connect the interior of the fluid port 38 with the region of the base 30 containing the projections 32.

In the present embodiment, the base 30 is a unitary member formed by injection molding, for example, with the filter support surface 31 being integrally formed with other portions of the base 30. However, it is also possible for the base 30 to comprise a plurality of separately formed components. For example, the filter support surface 31 may comprise a perforated plate, a porous plate, or a mesh which is removably installed within the interior of the base 30 and has an upper surface which can support the filter element 45.

The filter support surface 31 in the present embodiment is planar, but it may have any shape which enables to support the filter element 45 for filtration. For example, it may be dished, arched, or wave-like in shape The filter support surface 31 is surrounded by a circular wall 34 extending upwards from the outer periphery of the filter support surface 31, and a plurality of radial projections 35 extend upwards from a ledge formed atop the wall 34, with the vertical, radially inner surface of each projection 35 being flush with the wall 34. The wall 34 and the projections 35 serve to surround and position a filter element 45 disposed on the filter support surface 31.

It is convenient if the filtration assembly 10 is capable of standing upright on a level surface without being supported. In the present embodiment, the base 30 includes an outer wall 41 extending around its entire outer periphery for supporting the base 30 on a table or other level surface. The outer wall 41 does not need to perform a sealing function, so it need not be continuous around the periphery of the base 30 and it need not be fluid tight. Members other than a wall can also be used to support the base, such as a plurality of legs. Furthermore, it is not necessary for the base 30 to be self supporting, and it may have a shape which does not stand upright by itself. For example, the bottom of the base 30 may be shaped like a funnel.

The sample reservoir 20 and the base 30 may be separately formed but permanently connected to each other, or they may be formed as a single member. However, in the present embodiment, the sample reservoir 20 is detachably engaged with the base 30 so that the base 30 can be used separately from the sample reservoir 20 as part of a petri dish. The manner of engagement between the sample reservoir 20 and the base 30 is preferably such that the engagement creates a fluid-tight seal without the need for a sealing member, such as an O-ring or a gasket, yet such that the sample reservoir 20 and the base 30 can be readily disengaged from each other by hand. The lower end of the sample reservoir 20 is also preferably shaped so that a fluid-tight seal is formed between the sample reservoir 20 and the upper surface of a filter element 45 disposed on the filter support surface 31 to prevent fluid from the sample reservoir 20 from bypassing the filter element 45 by flowing between the sample reservoir 20 and the filter element 45.

In general, any type of detachable engagement providing intimate, sealing contact between the sample reservoir 20 and the base 30 around the entire inner periphery of the base 30 can be employed to detachably engage the two members. For example, there may be an interference fit between the sample reservoir 20 and the base 30 so that a radial force presses a peripheral surface of the sample reservoir 20 into sealing contact with an opposing peripheral surface of the base 30, or opposing surfaces of the sample reservoir 20 and the base 30 may be pressed into sealing contact with each other by a compressive force acting in the axial direction of the filtration assembly. In the present embodiment, the sample reservoir 20 and the base 30 are engaged with each other by an interference fit which produces a fluid-tight seal between the outer peripheral surface of the sample reservoir 20 and the inner peripheral surface of the base 30. The sample reservoir 20 and the base 30 may be structured so as to provide resistance to an axial force tending to pull them apart so as not to be inadvertently disconnected from each other during use. In the present embodiment, resistance to disengagement is provided by a snap fit in which the lower end of the sample reservoir 20 is received inside the upper end of the base 30. As shown in the cross-sectional elevation of FIG. 3, the lower end of the sample reservoir 20 has a groove 24 and a radially outward projection 25 which extend continuously around its entire outer periphery. Similarly, as shown in FIG. 4, the base 30 has a groove 36 and a radial inward projection 37 extending continuously around its entire inner periphery at its upper end. The outer diameter of the lower end of the sample reservoir 20 and the inner diameter of the base 30 are preferably selected so that the projections 25 and 37 will snap into and fit snugly inside the grooves 36 and 24, respectively, with an interference fit so that there is intimate contact, such as line contact or surface contact, between each projection and the corresponding groove around the entire circumference of the sample reservoir 20. The sample reservoir 20 on be disconnected from the base 30 simply by flexing the two members with respect to each other, for example, to disengage the projections from the grooves. It is generally easier to disengage the two members if the groove 36 and the projection 37 are formed as close to the upper end of the base 30 as possible. For example, in the present embodiment, projection 37 immediately adjoins the upper end of the base 30. The location of the sealing contact between the sample reservoir 20 and the base 30 is not critical as long as the contact can prevent fluid from leaking to the exterior of the filtration assembly 10 during normal use. For example, the sealing contact may be between the mating surfaces of the grooves 24, 36 and the projections 25, 38, or it could be formed in a different location, with engagement between the grooves and the projections serving primarily to resist inadvertent disengagement of the sample reservoir 20 and the base 30 or to maintain an axial compressive force between the sample reservoir 20 and the filter element 45 to form a fluid-tight seal against the filter element 45. In the latter case, the grooves and the projections need not be continuous members.

In the present embodiment, each groove is complementary in shape with the corresponding projection, i.e., it has substantially the same radius of curvature as the corresponding projection so that each groove and the corresponding projection are in surface contact, but the curvatures of the groove and the projection may be such that they are in line contact, for example. It is possible to form a seal between the sample reservoir 20 and the base 30 with a single projection formed on the surface of one of the two members and a single groove for engagement with the projection formed on the surface of the other two members, but a plurality of grooves and projections may create a seal of greater integrity.

Many other arrangements besides a snap fit can be used to resist disengagement between the sample reservoir 20 and the base 30, such as a bayonet fit or threaded engagement. It is also possible to dispose tape around the joint between the sample reservoir 20 and the base 30 or to lightly weld or bond the two members to each other (such as by ultrasonic welding) around their peripheries to secure the members together while enabling them to be easily disconnected from each other when desired. Such a manner of connection can be employed instead of or in addition to the interference fit provided by the grooves and projections on the sample reservoir 20 and the base 30.

The lower end of the sample reservoir 20 is formed with an annular sealing rim 26 which extends in generally the axial direction of the sample reservoir 20 around the entire periphery of the sample reservoir 20. When the grooves and the projections of the sample reservoir 20 and the base 30 are engaged with each other, the sealing rim 26 is pressed downwards into sealing contact with the upper surface of the filter element 45 disposed atop the filter support surface 31 of the base 30. The compressive force between the sealing rim 26 and the filter element 45 is maintained by the engagement between the grooves and the projections of the sample reservoir 20 and the base 30. In the present embodiment, the sealing rim 26 is positioned on the sample reservoir 20 such that an annular air space is present between the outer periphery of the sealing rim 26 and the inner periphery of the base 30 around the entire circumference of the sealing rim 26. It is thought that the air space may improve the integrity of the seal between the sample reservoir 20 and the base 30 by forming an air lock which prevents creeping of fluid by capillary action between the two members. However, the air space is not essential, and the sealing rim 26 may closely contact the inner periphery of the base 30.

While the filter support surface 31 is part of the base 30 in the present embodiment, it is also possible for the filter support surface to be part of the sample reservoir 20. For example, instead of the sample reservoir 20 being completely open at its lower end, it may have a perforated bottom surface for supporting a filter element 45, and the base 30 may function as a funnel located beneath the sample reservoir 20 to collect filtrate which has passed through the bottom surface of the sample reservoir 20.

The filter element 45 comprises a filter medium capable of removing microorganisms of interest from the fluid being filtered. The filter medium may be of any desired type, such as a microporous membrane of various materials, or filter paper, for example. A wide variety of filter media for microbiological studies are commercially available, and any such filter media can be employed with the present invention as the filter element 45. Filter media for use in microbiological studies are frequently flat membrane discs, but the filter element 45 need not have any particular shape. For example, instead of being flat, it may have pleats to increase its surface area.

The filter element 45 may directly contact the filter support surface 31 of the base 30, or it may rest upon an intermediate support member, such as a layer of mesh, paper, or fabric which is more porous than the filter element 45 and which provides mechanical support to the filter element 45. When the filter element 45 is to be left on the base 30 during incubation, it may be convenient if an absorbent pad 46 for use in holding a nutrient solution during incubation is placed beneath the filter element 45 prior to filtration rather than afterwards to reduce the amount of handling of the filter element 45 after filtration. Furthermore, the absorbent pad 46 can provide support for the filter element 45 during filtration. It is also possible to place a prefilter, a protective sheet, or other member atop the filter element 45.

It may be advantageous to place a resilient, compressible member between the lower surface of the filter element 45 and the filter support surface 31 in the region beneath where the sealing rim 26 contacts the filter element 45. Such a member can compensate for variations in the axial length of the sealing rim 26 or in the smoothness of the opposing surfaces of the sealing rim 26 and the filter support surface 31 to maintain the sealing rim 26 in intimate, sealing contact with the filter element 45, thereby enabling the manufacturing tolerances of the sample reservoir 20 and the base 30 to be less precise. The resilient member may be either permeable or impermeable to the fluid being filtered. For example, it may comprise a porous sheet or pad, and in the present embodiment, the absorbent pad 46 serves as the resilient member. Alternatively, the resilient member may comprise an impermeable gasket disposed beneath the filter element 45. It is also possible to place a resilient sealing member, such as a gasket, between the top surface of the filter element 45 and the sealing rim 26 so that the sealing rim 26 does not directly contact the filter element 45 but is pressed into sealing contact with the sealing member, which in turn is pressed into sealing contact with the filter element 45. Such a sealing member may be separate from or joined to the filter element 45.

In the present embodiment, the wall 34 surrounding the filter support surface 31 preferably has a height such that when an absorbent pad 46 and a filter element 45 are mounted on the filter support surface 31, the absorbent pad 46 will be surrounded by the wall 34 and disposed at least partially below the upper end of the wall 34, while the filter element 45 disposed atop the filter element 45 will be positioned at or above the upper end of the wall 34 and will be surrounded by the radial projections 35. For example, the wall 34 may have a height substantially the same as the thickness of the absorbent pad 46. With the absorbent pad 46 located partially or entirely below the upper end of the wall 34, when a user of the filtration assembly 10 wishes to transfer the filter element 45 from atop the absorbent pad 46 to a different location, it is easy for the user to pick up the filter element 45 using forceps without picking up the absorbent pad 46 as well. The spaces between the radial projections 35 provide easy access to the filter element 45 and facilitate its removal from the base 30.

Figure 2:
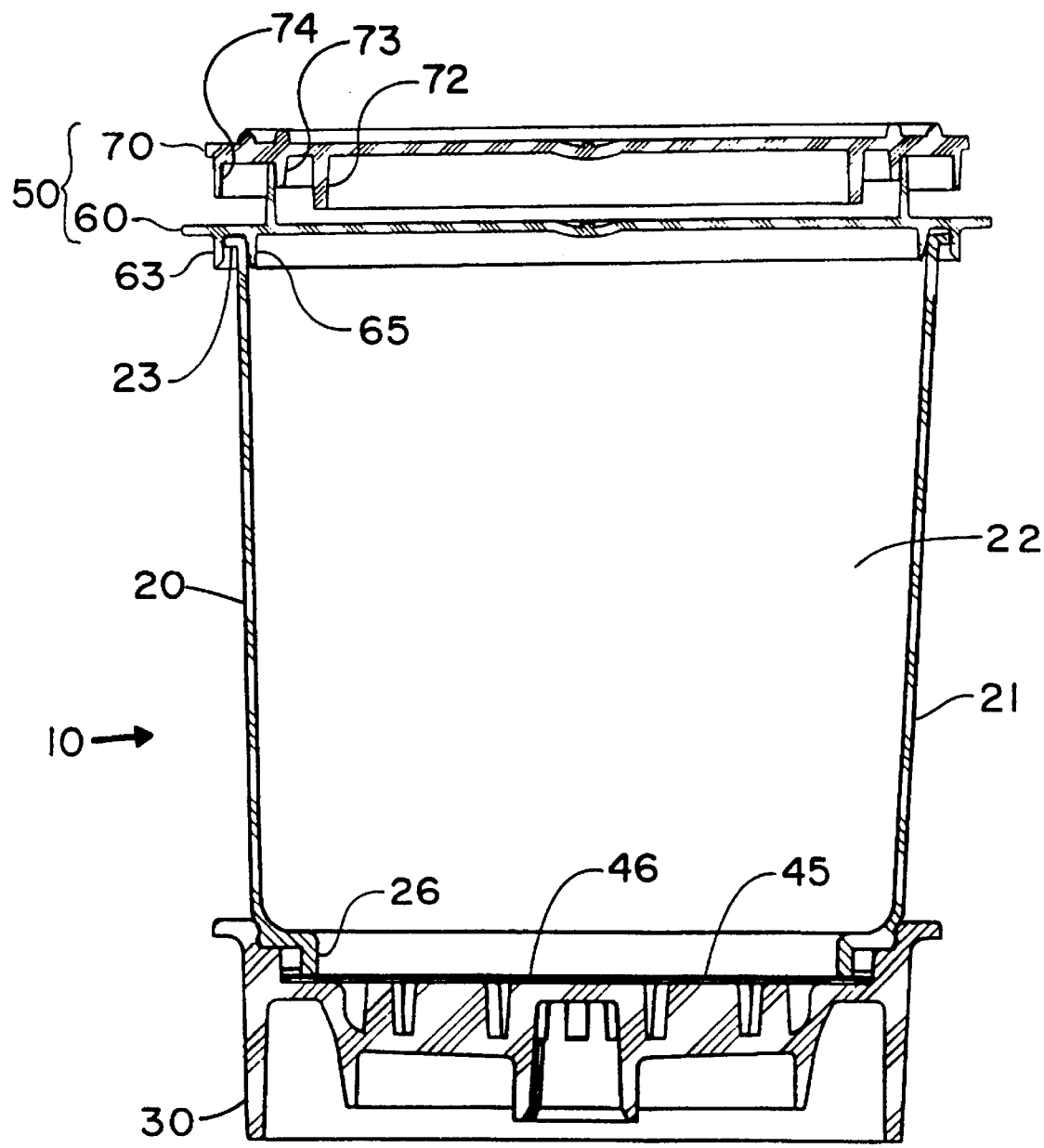
FIG. 2 is a vertical cross-sectional view of the embodiment of FIG. 1.
Figure 3:
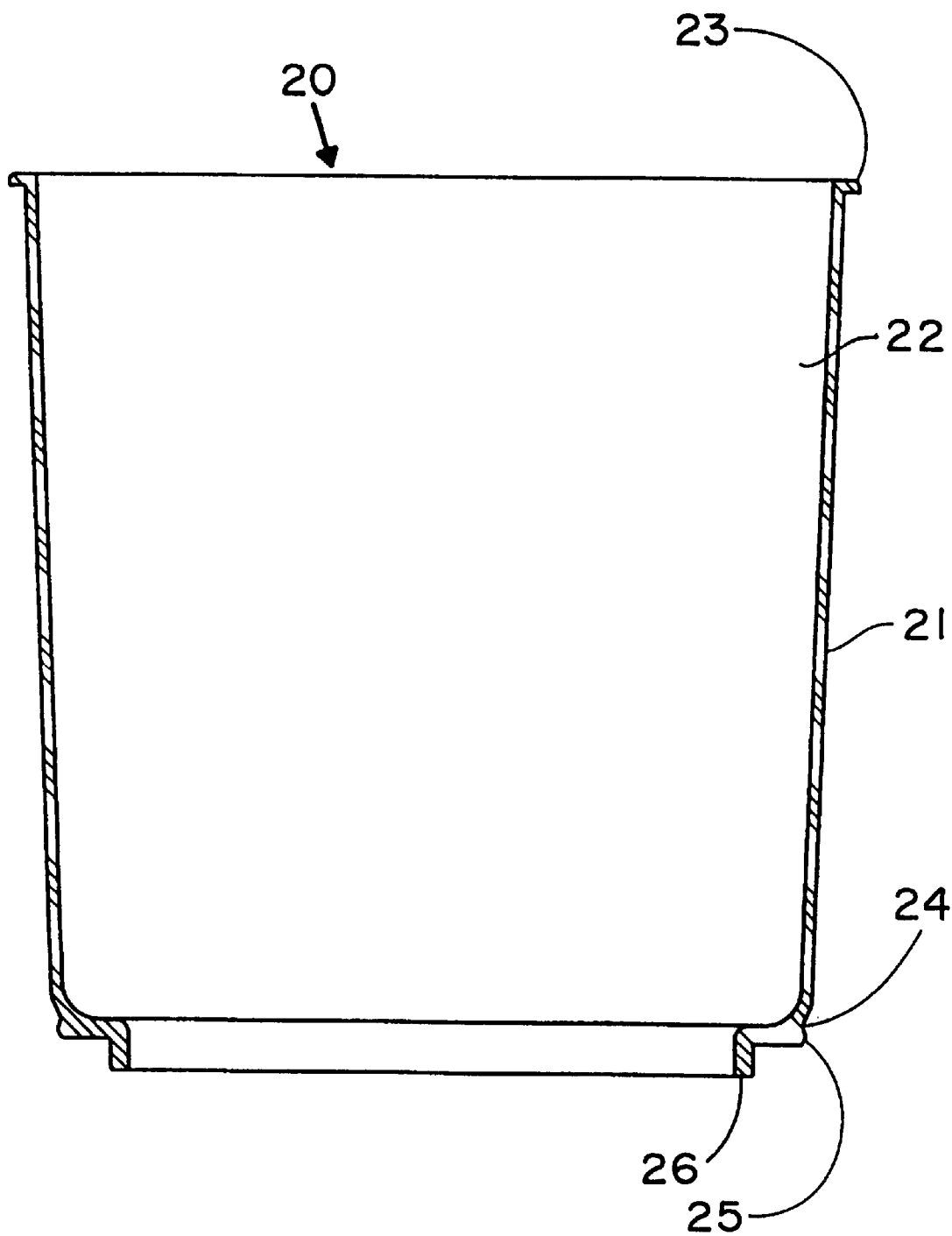
FIG. 3 is a vertical cross-sectional view of the sample reservoir of the embodiment of FIG. 1.

From the standpoint of ease of manufacture, it is preferable if the axial length of the sealing rim 26 of the sample reservoir 20 and the axial height of the radial projections 35 on the base 30 are such that when the sample reservoir 20 sealingly engages the base 30 and the sealing rim 26 of the sample reservoir 20 is pressed into sealing contact with the filter element 45 as shown in FIG. 2, there is an axial gap between the top surface of the radial projections 35 and the bottom surface of the sample reservoir 20. If such a gap is present, the radial projections 35 and the sealing rim 26 do not need to be manufactured to as precise tolerances as when the upper surfaces of the radial projections 35 contact the bottom surface of the sample reservoir 20.

Figure 7:
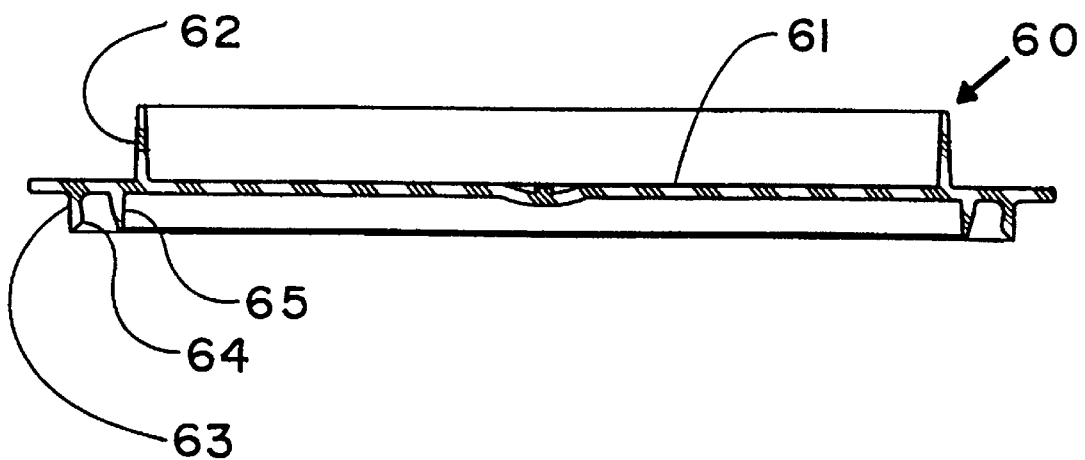
FIG. 7 is a vertical cross-sectional view of the lower cover of the embodiment of FIG. 1.
Figure 8:
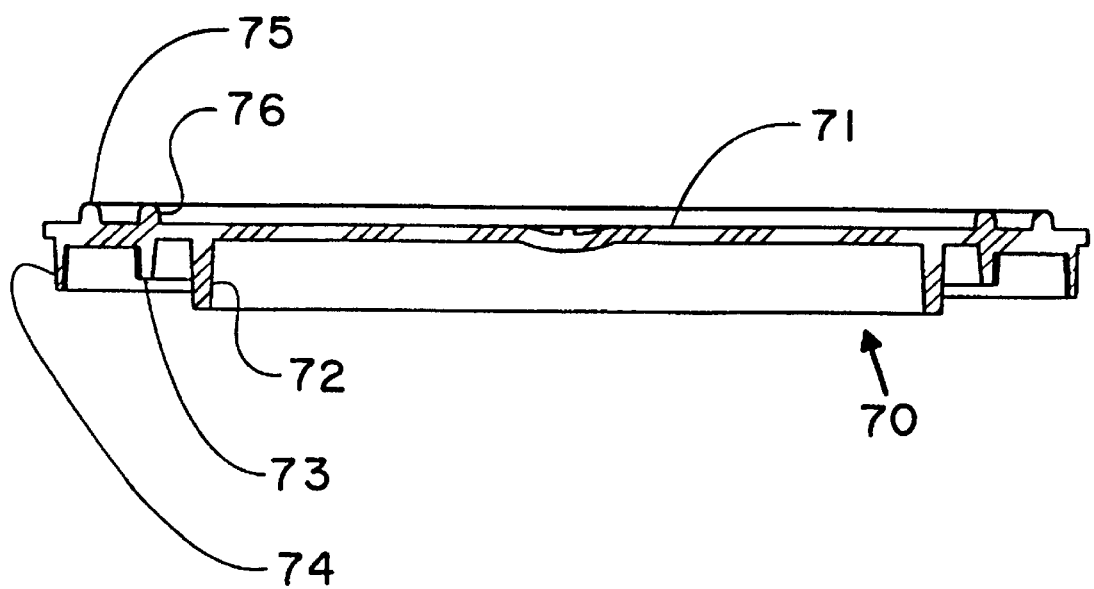
FIG. 8 is vertical cross-sectional view of the upper cover of the embodiment of FIG. 1.

The cover assembly 50 comprises a lower cover 60 and an upper cover 70, which are best illustrated in FIGS. 7 and 8, respectively. The lower cover 60 is shaped so as to detachably fit atop the upper end of the sample reservoir 20, and the upper cover 70 is shaped so as to detachably fit atop the lower cover 60 or to detachably fit atop the upper end of the base 30, thereby enabling the covers 60, 70 to together form a petri dish and enabling the upper cover 70 and the base 30 to together form another petri dish. The upper cover 70 may also be shaped so as to detachably fit directly atop the upper end of the sample reservoir 20 with the lower cover 60 removed.

The lower cover 60 may engage with the upper end of the sample reservoir 20 in various manners. For example, they may engage each other with a snap fit, a bayonet fit, threaded engagement, a press fit, or a loose fit. Preferably, the engagement is such as to provide some resistance to disengagement of the lower cover 60 from the sample reservoir 20 so as to enable the filtration assembly 10 to be handled and transported without the cover assembly 50 falling off the sample reservoir 20, while still permitting the lower cover 60 to be readily detached from the sample reservoir 20. In the present embodiment, the lower cover 60 comprises a disc-shaped plate 61 having a continuous annular projection 62 extending upwards from its upper surface. When the cover assembly 50 is used as a petri dish, the projection 62 serves as an outer wall of the petri dish. The plate 61 also has a continuous annular projection 63 extending from its lower surface. A snap fit is formed between the annular projection 63 and a radially outward lip 23 formed around the entire outer periphery of the upper end of the sample reservoir 20. The projection 63 on the lower cover 60 has a radially inward bulge 64. The minimum inner diameter of the lower cover 60 measured at the bulge 64 in a relaxed (unstressed) state is smaller than the outer diameter of the sample reservoir 20 at the lip 23 in a relaxed state so that when the lip 23 is urged upwards past the bulge 64, the bulge 64 will resist disengagement of the sample reservoir 20 and the lower cover 60. The engagement between the lower cover 60 and the sample reservoir 20 may be of varying degrees of tightness. For example, the engagement may be sufficient to provide some resistance to disengagement without forming a seal, or the engagement may provide a fluid-tight seal between the two members. A fluid-tight seal between the lower cover 60 and the sample reservoir 20 is convenient when the sample reservoir 20 is to be used for temporary storage of a fluid sample prior to filtration. For example, in factories, it is common to collect a fluid sample in one part of the factory and then to carry the sample to a laboratory for analysis in a different part of the factory. In such cases, the provision of a fluid-tight seal between the cover assembly 50 and the sample reservoir 20 enables a fluid sample within the sample reservoir 20 to be transported from one location to another without fear of spilling or contamination, A fluid-tight seal can be formed by any suitable means, but preferably by one which does not require the use of a separate sealing member, such as an O-ring or a gasket. In the present embodiment, a fluid-tight seal is achieved between the lower cover 60 and the sample reservoir 20 with the assistance of an annular projection 65 which extends downwards from the lower surface of the lower cover 60. The outer diameter of the projection 63 in a relaxed state is larger than the inner diameter of the upper end of the sample reservoir 20 in a relaxed state so that when the lip 23 of the sample reservoir 20 is placed into the space between the two projections 63 and 65, the upper end of the sample reservoir 20 will be urged radially outwards by the inner projection 65 towards projection 63. The upper end of the sample reservoir 20 is thereby pressed into intimate contact with at least projection 65 and possibly both projections 63 and 65, resulting in the formation of a fluid-tight seal between the lower cover 60 and the sample reservoir 20 around the entire periphery of the sample reservoir 20 somewhere in the space between the two projections 63 and 65.

The upper cover 70 likewise comprises a disc-shaped plate 71. The plate 71 has a plurality of annular projections 73, 74 extending downwards from its lower surface. A first projection 73 has an outer diameter so as to engage with the inner periphery of the projection 62 on the top surface of the lower cover 60.

Like the fit between the lower cover 60 and the upper end of the sample reservoir 20, the fit between the lower and upper covers 60 and 70 where they engage at projections 62 and 73 may have varying degrees of tightness, varying from a fluid-tight fit to a loose fit. In the present embodiment, projection 73 on the upper cover 70 snugly engages the inner surface of projection 62 of the lower cover 60 to prevent the upper cover 70 from being inadvertently dislodged from the lower cover 60 during handling but permitting the upper cover 70 to be easily removed from the lower cover 60 by hand when desired. Projection 73 need not extend continuously around the upper cover 70, particularly when it does not need to seal against projection 62 on the lower cover 60.

Figure 10:
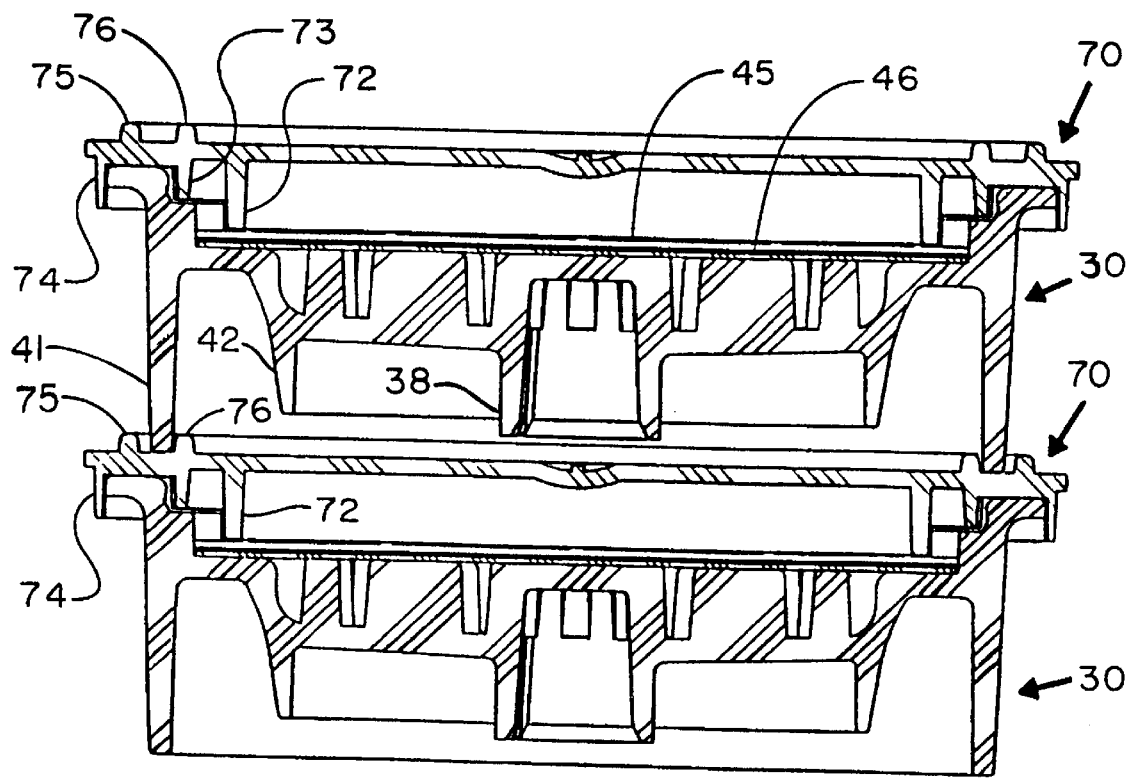
FIG. 10 is a vertical cross-sectional view of two petri dishes stacked atop each other, each petri dish comprising a base and an upper cover like those of the embodiment of FIG. 1.

The lower cover 60 has another annular projection 74 which extends downwards from its lower surface concentric with and surrounding projection 73 As shown in FIG. 10, the upper cover 70 can be placed atop the upper end of the base 30 to serve as a cover for the base 30, with the upper cover 70 and the base 30 together forming a petri dish. The inner diameter of projection 74 is selected so that the inner surface of projection 74 can snugly engage the outer peripheral surface of the base 30 to prevent the upper cover 70 from falling off the base 30 during handling or when the base 30 and the upper cover 70 are inverted. In this embodiment, the engagement between projection 73 and the outer periphery of the base 30 does not form a seal. However, a looser or tighter fit between the upper cover 70 and the base 30 (including a fit forming a fluid-tight seal) is possible.

When the cover assembly 50 is used as a petri dish, a filter element 45 and an absorbent pad 46 are typically placed in the space between the two covers 60 and 70, and the covers are placed in an incubator to culture microorganisms present on the filter element 45. The absorbent pad 46 placed between the covers is usually a different absorbent pad from the one which may be placed beneath the filter element 45 during filtration (although they may be identical to each other) so that the user does not need to transfer a wet absorbent pad from one location to another. In accordance with one method of culturing which may be employed, the petri dish defined by the cover assembly 50 is stored right-side up during incubation with the filter element 45 and absorbent pad 46 resting on the top interior surface of the lower cover 60. However, in accordance with another method of culturing which may be employed, the petri dish is stored upside down during incubation with the lower cover 60 positioned atop the upper cover 70 and with the filter element 45 and absorbent pad 46 pressed against the interior surface of the lower cover 60. To facilitate the use of the cover assembly 50 with this second culturing method, the upper cover 70 may be equipped with a retaining member on its lower surface for retaining a filter element 45 and absorbent pad 46 against the top surface of the lower cover 60, with the weight of the filter element 45 and the absorbent pad 46 supported by the retaining member, when the cover assembly 50 is inverted. In the present embodiment, the retaining member comprises a projection 72 in the shape of an annular wall which extends downwards from the lower surface of the upper cover 70 towards the lower cover 60. When the upper surface of projection 62 of the lower cover 60 abuts against the bottom surface of the upper cover 70, the distance between the bottom surface of projection 72 and the top surface of the lower cover 60 is such that a filter element 45 and an absorbent pad 46, if present, can be pressed against the top surface of the lower cover 60 by projection 72 and be prevented from falling down when the cover assembly 50 is inverted. Projection 72 does not need to form a seal against the filter element 45, so it does not need to extend continuously around the entire periphery of the filter element 45. Furthermore, a retaining member need not be in the shape of a wall. For example, it could be in the form of a plurality of pins or other projections extending downwards from the upper cover 70 towards the lower cover 60. Preferably, the retaining member contacts the filter element 45 near the outer periphery of the filter element 45 so as to minimize interference with the growth of microorganisms on the filter element 45, but if the filter element 45 is particularly heavy and needs support at locations other than around its periphery, the retaining member may contact the filter element 45 in locations other than the periphery. When the upper cover 70 is mounted atop the base 30, the retaining member functions in a similar manner to retain a filter element and absorbent pad 46 against the filter support surface 31 of the base 30 when the upper cover 70 and base 30 are inverted. In situations in which the cover assembly 50 or the upper cover 70 and the base 30 are not expected to be inverted during culturing, the retaining member may be omitted. It is also possible to employ a retaining member which is formed separately from the upper cover 70, such as a ring which can be inserted between the two covers 60 and 70 where projection 72 is formed in the present embodiment so as to be pressed against the top surface of a filter element 45.

Figure 9:
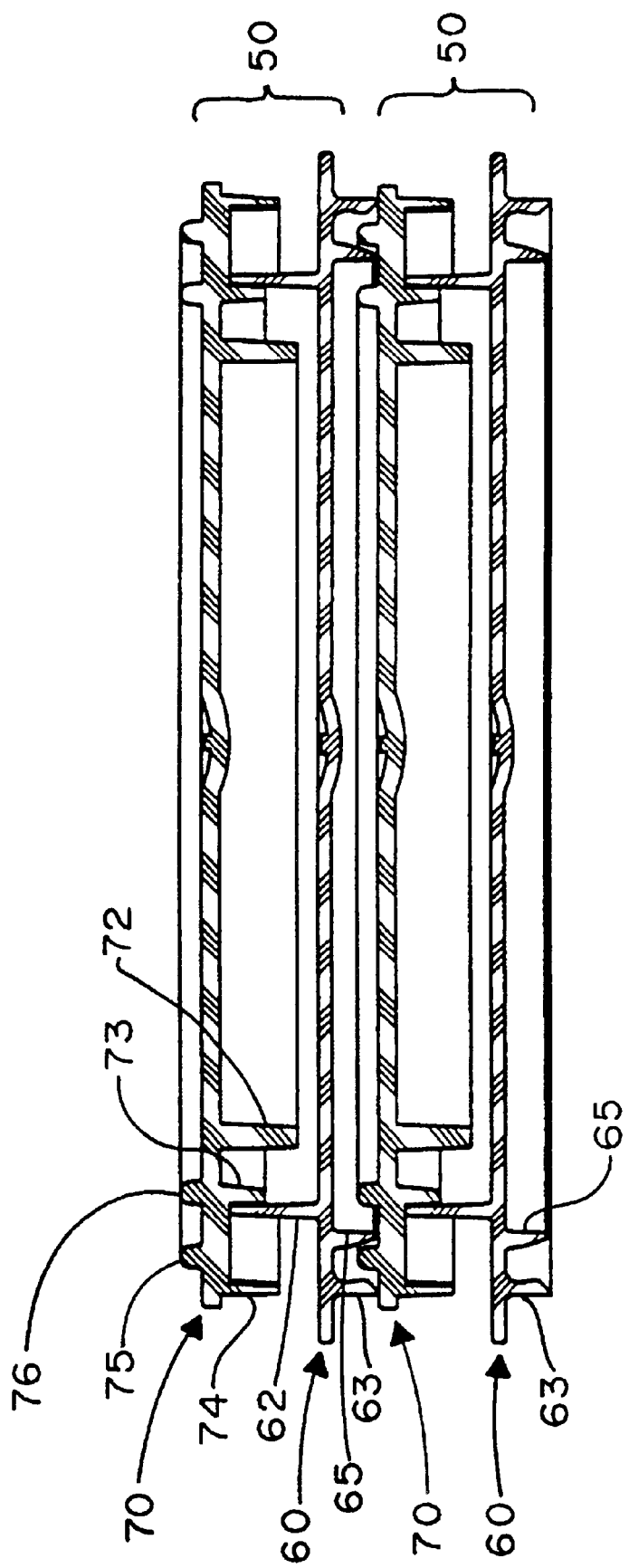
FIG. 9 shows two petri dishes stacked atop each other, each petri dish comprising a cover assembly like that of the embodiment of FIG. 1.

In order to save space, a plurality of petri dishes are typically stacked atop each other during incubation of microorganisms in the petri dishes. The present embodiment is arranged so that a plurality of petri dishes (each comprising one of the cover assemblies or else comprising an upper cover 70 and a base 30) can be stacked atop each other. FIG. 9 is a vertical cross-sectional view of two petri dishes, each comprising a cover assembly 50, stacked atop each other. In this figure, projections 63 and 65 on the bottom surface of each lower cover 60 rest atop the top surface of the upper cover 70 of the cover assembly 50 located below it. If the stack of petri dishes is inverted, the top surface of each upper cover 70 rests atop projections 63 and 65 on the bottom surface of the lower cover 60 of the cover assembly 50 located below it. FIG. 10 is a vertical cross-sectional view of two petri dishes, each comprising a base 30 and an upper cover 70, stacked atop each other. The outer wall 41 of each base 30 rests on the upper surface of the upper cover 70 of another petri dish located beneath it. Alternatively, if the petri dishes are inverted, the upper surface of each upper cover 70 rests atop the outer wall 41 of the base 30 of the petri dish located beneath it. Any number of petri dishes can be stacked atop each other in the manner shown in FIGS. 9 and 10. Furthermore, a stack of petri dishes can contain one or more petri dishes like those shown in FIG. 9 along with one or more petri dishes like those shown in FIG. 10. In order to give a stack of petri dishes greater stability, each upper cover 70 may be equipped with a stabilizing structure which can resist lateral movement of an adjoining petri dish to prevent one petri dish from inadvertently being knocked off the petri dish located below it. In the present embodiment, the stabilizing structure comprises two annular ridges 75 and 76 which extend upwards from the top surface of the upper cover 70. When the lower cover 60 of one petri dish sits on the upper cover 70 of another petri dish, the outer annular ridge 75 of the upper cover 70 is located between the two projections 63 and 65 on the lower surface of the lower cover 60. When a lateral force is applied to one of the covers, the outer annular ridge 75 on the upper cover 70 contacts one or both of projections 63 and 65 on the lower cover 60 to resist relative lateral movement of the two covers. As shown in FIG. 10, when the base 30 of one petri dish sits on the upper cover 70 of another petri dish, the outer wall 41 of the base 30 contacts the upper cover 70 between the two annular ridges 75 and 76, and lateral movement of the outer wall 41 relative to the upper cover 70 is resisted by one or both of the ridges. It is not necessary for the ridges 75, 76 to form a seal against the portion of another petri dish which they contact, so they need not be continuous and they need not tightly engage the adjoining petri dish. Furthermore, a stabilizing structure is not restricted to the form of ridges. For example, a stabilizing structure could be in the form of pins, bumps, tabs, or other projections on the top surface of the upper cover 70, or it could be in the form of a recess formed in the top surface of the upper cover 70 for receiving one or both of the projections 63 and 65 on the lower cover 60 or the outer wall 41 of the base 30.

The filtration assembly 10 can be made from a wide variety of materials, including those conventionally used for funnels, reservoirs, petri dishes, and other laboratory equipment, such as metals, plastics, and glass, depending upon factors such as the desired strength, flexibility, heat resistance, and corrosion resistance and upon whether the filtration assembly 10 is intended to be reusable or discarded at the completion of use. Different portions of the filtration assembly 10 may be formed of different materials. For economy of manufacture, plastics which can be shaped by molding are particularly suitable for the filtration assembly 10. Some examples of suitable plastics are polypropylene, nylon, and polyacrylate. In some instances, it is convenient if portions of the assembly 10, such as one or both of the lower and upper covers 60 and 70, are translucent or transparent to permit substances within the assembly 10 to be readily observed.

Figure 11:
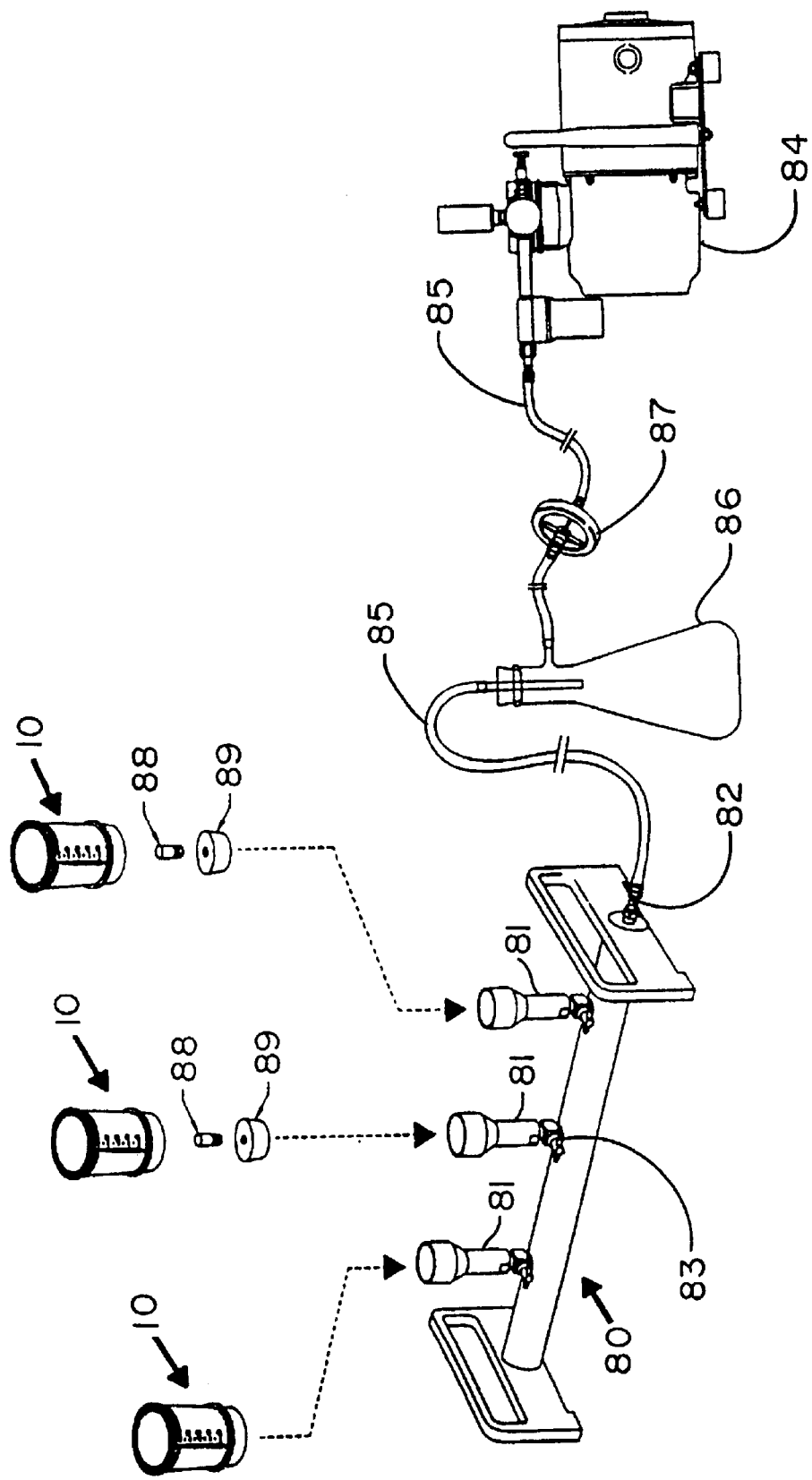
FIG. 11 illustrates a vacuum filtering arrangement with which the embodiment of FIG. 1 can be used.
Figure 12:
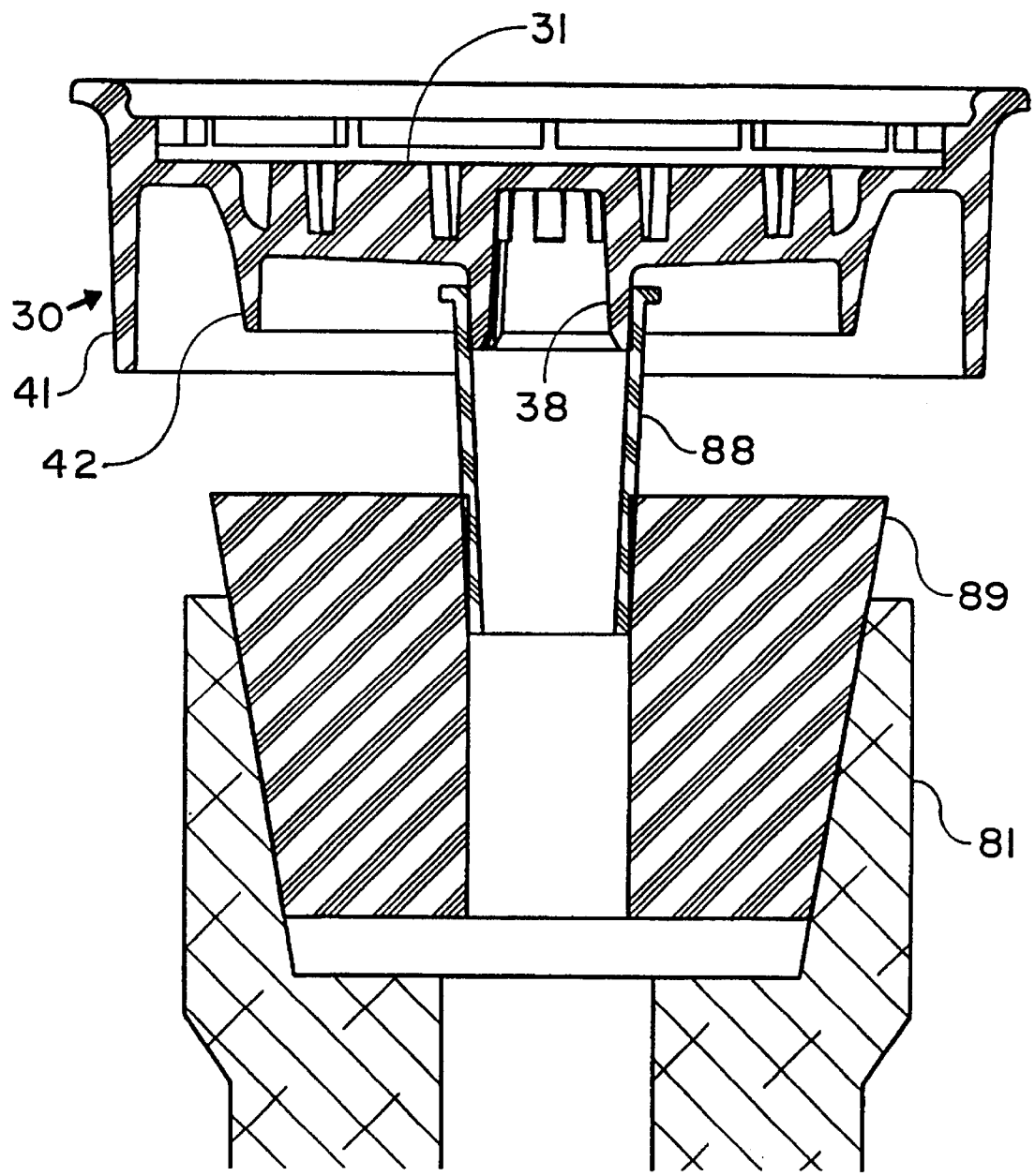
FIG. 12 is a vertical cross-sectional view of the base of the embodiment of FIG. 1 installed on a vacuum manifold using an adapter and a stopper.
Figure 13:
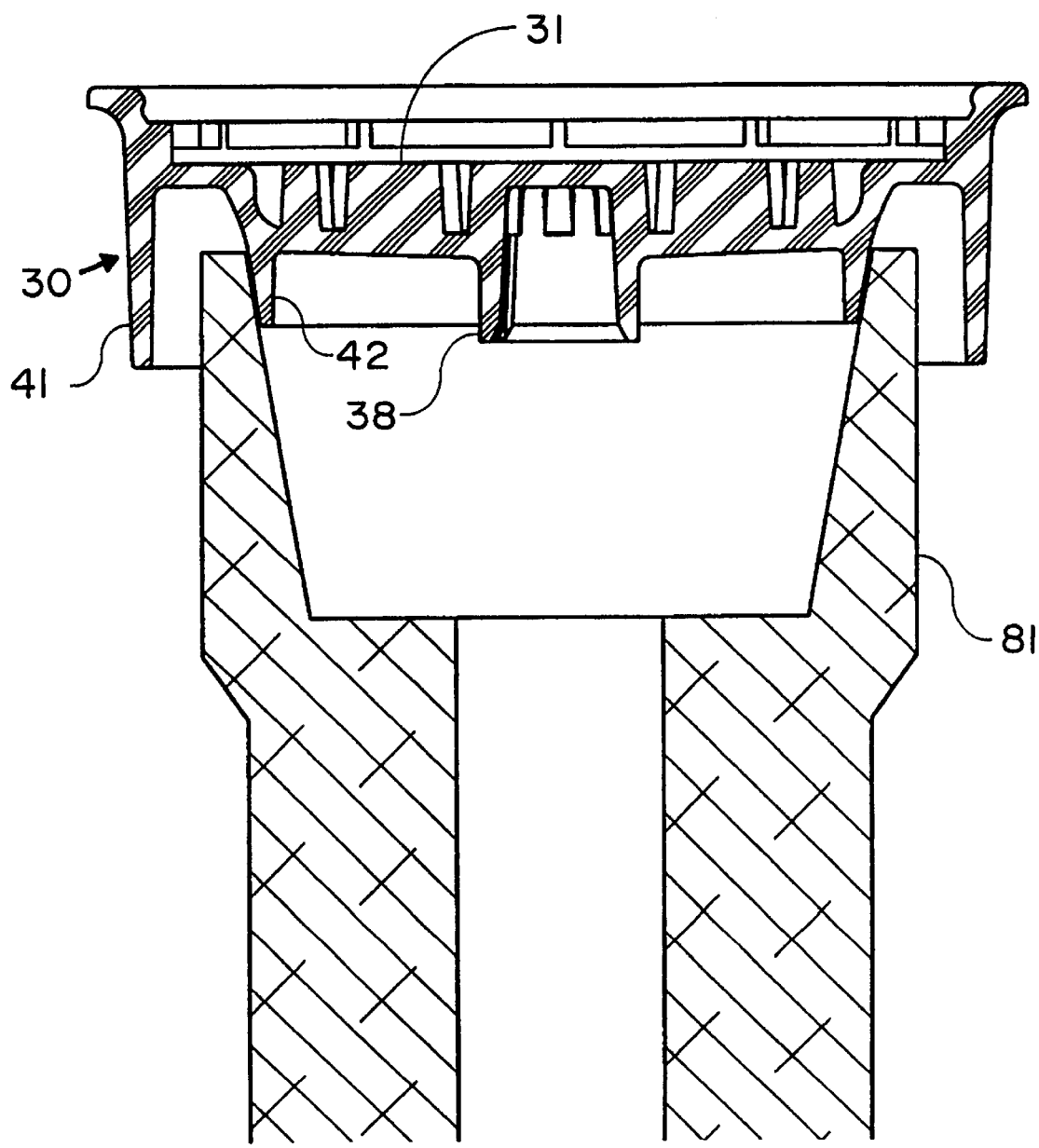
FIG. 13 is a vertical cross-sectional view of the base of the embodiment of FIG. 1 directly engaging a vacuum manifold for vacuum filtration.

Filtration of a fluid sample in the sample reservoir 20 can be performed by a variety of conventional methods, including gravity filtration and vacuum filtration. In vacuum filtration, the filtration assembly 10 is mounted on a vacuum manifold, a filtration flask, or other device through which suction can be applied to the fluid port 38 to suck fluid in the sample reservoir 20 through the filter element 45 and out of the fluid port 38. FIG. 11 is a schematic view of a vacuum filtration arrangement with which a filtration assembly 10 according to the present invention can be employed. The illustrated arrangement includes a vacuum filtration manifold 80 having a plurality of inlet tubes 81, each of which can support a filtration assembly 10. Any one of the inlet tubes 81 can be fluidly connected through the interior of the manifold 80 to a vacuum port 82 of the manifold 80 by a stopcock 83. Suction can be applied to the vacuum port 82 by a vacuum pump 84 connected to it by a hose 85. Depending on the structure of the pump 84, a vacuum filtration flask 86 and a filter 87 for removing aerosols from air may be installed between the manifold 80 and the pump 84 to prevent the fluid being filtered from being sucked into the pump 84. In order to perform filtration with this arrangement, a filtration assembly 10 containing a filter element 45 and possibly an absorbent pad 46 disposed on the filter support surface 31 of the base 30 is mounted on one of the inlet tubes 81 with the fluid port 38 of the base 30 fluidly communicating with the inlet tube 81. The fluid port 38 may be connected to one of the inlet tubes 81 in a variety of manners. One way, schematically shown in FIG. 12, is to insert the fluid port 38 into the upper end of a hollow adapter 88 and to insert the lower end of the adapter 88 into the bore of a hollow rubber stopper 89 sized to fit into the upper end of one of the inlet tubes 81. The adapter 88, which may be either a rigid or flexible member, is sized so as to form line or surface contact with the outer surface of the fluid port 38 when the fluid port 38 is inserted into the adapter 88 with a sufficiently tight fit between the fluid port 19 and the adapter 88 to obtain a desired suction in the fluid port 38 when the vacuum pump 84 is operated. Alternatively, as schematically shown in FIG. 13, the base 30 of the filtration assembly 10 may also be shaped so as to directly engage with the inlet tube 81 of the manifold 80 without the need for an adapter 88 or a stopper 89. In this embodiment, the base 30 includes an annular skirt 42 disposed between the fluid port 38 and the outer wall 41 and extending downwards from the lower surface of the base 30. The outer periphery of the skirt 42 is shaped so as to be in line contact or surface contact with the inner surface of the inlet tube 81 around its entire periphery when the skirt 42 is inserted into the inlet tube 81. The skirt 42 may but need not form a fluid-tight seal against the inlet tube 81. The skirt 42 preferably engages the inlet tube 81 sufficiently tightly that the vacuum pump 84 can generate sufficient suction in the inlet tube 81 to suck fluid contained in the sample reservoir 20 through the filter element 45. It may be easier to obtain a desired fit between the skirt 42 and the inlet tube 81 if the skirt 42 is somewhat flexible. The skirt 42 may also be shaped to directly contact filtration equipment other than an inlet tube of a vacuum filtration manifold, such as the mouth of a filtration flask. Either before or after the assembly 10 is mounted on the inlet tube 81, a desired quantity of a fluid sample to be filtered is placed into the sample reservoir 20. With the filtration assembly 10 mounted on one of the inlet tubes 81, the vacuum pump 84 is operated to suck the fluid sample through the filter element 45 and into the filtration flask 86. During operation of the pump 84, the cover assembly 50 is usually removed from the sample reservoir 20 so that the interior of the sample reservoir 20 above the fluid being filtered will be at atmospheric pressure, thereby making filtration easier and preventing suction generated by the pump 84 from causing the sample reservoir 20 to collapse. When the fluid sample has been sucked out of the sample reservoir 20 and through the filter element 45, the pump 84 is turned off. At this time, the filtration assembly 10 may be removed from or left mounted on the vacuum manifold 80. When the cover assembly 50 is to be used as a petri dish, an absorbent pad 46 is placed atop the lower cover 60 within the region surrounded by annular projection 62, and a suitable nutrient solution for culturing microorganisms is applied to the absorbent pad 46 in a conventional manner. The sample reservoir 20 is then detached from the base 30 by hand and the filter element 45 is removed from atop the base 30 with forceps, for example, and placed atop the absorbent pad 46 on the lower cover 60. The upper cover 70 is then placed atop the lower cover 60 to form a petri dish, and the microorganisms in the petri dish are incubated in a suitable manner, such as by being placed into a conventional incubator. Incubation of a single petri dish may be performed, or a plurality of petri dishes can be stacked atop each other during incubation as shown in FIG. 10.

Figure 14:
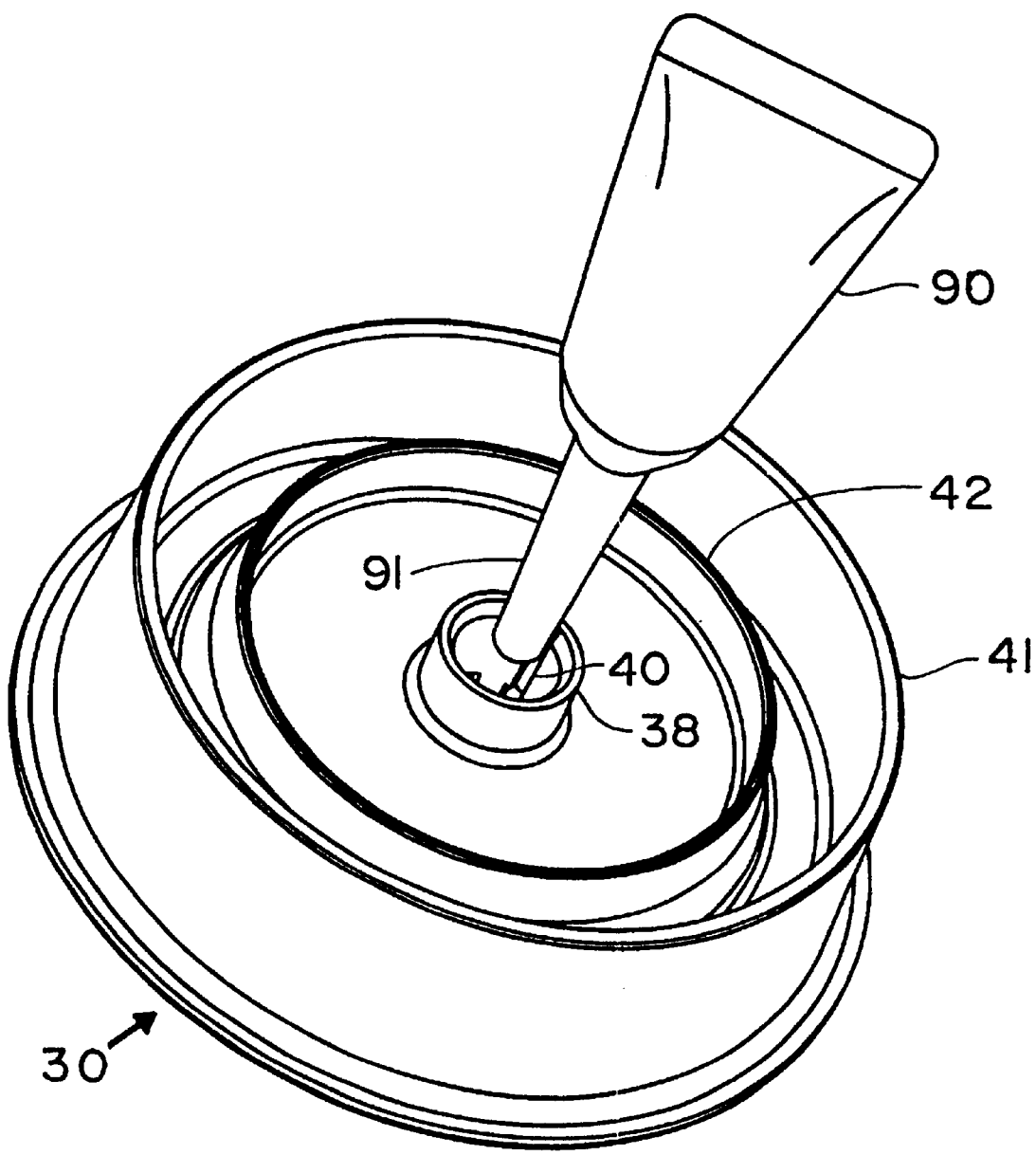
FIG. 14 is a bottom isometric view of the base illustrating a method of introducing a nutrient solution through the fluid port of the base.

If the base 30 and the upper cover 70 are instead to be used as a petri dish, after the completion of filtration, the sample reservoir 20 is detached by hand from the base 30 by releasing the snap fit between them, and the filter element 45 is left atop the base 30 while a suitable nutrient solution is applied to the absorbent pad 46 located beneath the filter element 45, the absorbent pad 46 typically having been placed beneath the filter element 45 prior to filtration. The nutrient solution can be applied to the absorbent pad 46 either from above, through the filter element 45, or from below via the fluid port 38. A method of introducing the solution through the fluid port 38 is shown in FIG. 14. The nutrient solution is usually contained in an ampule 90 having a tapered snout 91 which can be inserted into the fluid port 38 and from which the nutrient solution can be dispensed. Since the fit between the outer surface of the snout 91 of the ampule 90 and the inner surface of the fluid port 38 may be fairly tight, one or more air vents 40 may be formed in the fluid port 38 to enable air to escape from the fluid port 38 when the outer surface of the snout 91 of the ampule 90 is pressed tightly against the inner surface of the fluid port 38 to prevent the formation of an air lock which could impede the introduction of the nutrient solution into the fluid port 38. In the present embodiment, the fluid port 38 has three air vents 40, each comprising an elongated groove formed in the inner periphery of the fluid port 38 between the openings 39 in the fluid port 38 and its outer end. When the nutrient solution is being applied to the absorbent pad 46 through the fluid port 38, the sample reservoir 20 or the upper cover 70 may be mounted on the base 30 to prevent the filter element 45 and absorbent pad 46 from falling off. Once the nutrient solution has been applied to the absorbent pad 46 and the upper cover 70 is mounted on the base 30, the petri dish comprising the base 30 and the upper cover 70 are ready to be incubated. If desired, a closure, such as a cap or a plug, may be mounted on the lower end of the fluid port 38 to prevent fluid from leaking out of it during incubation. If the base 30 is disposed upside down during incubation with the fluid port 38 facing upwards, a closure may be unnecessary.

In general, a petri dish comprising the cover assembly 50 and a petri dish comprising the base 30 and the upper cover 70 are both highly satisfactory. However, in some situations, one type of petri dish may have advantages over the other. For example, it may be more convenient to use a petri dish comprising the base 30 and the upper cover 70 because it is not necessary to remove the filter element 45 from the base 30 at the completion of filtration, resulting in fewer steps to be performed and less wear on the filter element 45. On the other hand, at the completion of filtration, the absorbent pad 46 beneath the filter element 45 on the base 30 may be saturated with filtrate. If the presence of the filtrate in the absorbent pad 46 is objectionable or if the filtrate excessively dilutes the nutrient solution which is added to the absorbent pad 46 in order for culturing to take place, it may be desirable to instead use the cover assembly 50 as a petri dish, since an absorbent pad 46 within the cover assembly 50 will not have been exposed to fluid during filtration.

What is claimed is:

1. A filtration assembly comprising:
a chamber for holding a fluid sample to be filtered;
a fluid port for filtrate in fluid communication with the chamber;
a filter support surface for supporting a filter element on a flow path between the chamber and the fluid port; and
a cover assembly including a lower cover detachably covering the chamber and an upper cover detachably mounted on the lower cover, the cover assembly defining a petri dish into which a filter element can be placed for cultivating microorganisms present on the filter element.

2. A filtration assembly as claimed in claim 1 including a sample reservoir defining the chamber and a base supporting the sample reservoir and comprising the fluid port, one of the sample reservoir and the base comprising the filter support surface, the lower cover being detachably mounted on the sample reservoir.

3. A filtration assembly as claimed in claim 2 wherein the base comprises the filter support surface.

4. A filtration assembly as claimed in claim 2 wherein the lower cover engages the sample reservoir with a snug fit.

5. A filtration assembly as claimed in claim 2 wherein the lower cover engages the sample reservoir with a fluid-tight fit without using a sealing member.

6. A filtration assembly as claimed in claim 2 wherein the sample reservoir is detachable from the base and one of the covers of the cover assembly can be detachably mounted on the base to define a petri dish with the base.

7. A filtration assembly as claimed in claim 6 wherein the one of the covers can engage the base with a fit such that the base can be inverted without the one of the covers being detached from the base.

8. A filtration assembly as claimed in claim 1 wherein the upper and lower covers engage each other with a fit such that the cover assembly can be inverted without the upper and lower covers being detached from each other.

9. A filtration assembly as claimed in claim 1 wherein the upper cover includes a retaining member for retaining a filter element disposed between the upper and lower cover against the lower cover when the cover assembly is inverted with the lower cover above the upper cover.

10. A filtration assembly as claimed in claim 1 wherein the upper cover includes a stabilizing structure on an upper surface thereof for resisting lateral movement of an identical cover assembly when stacked atop the upper cover.

11. A filtration assembly as claimed in claim 10 wherein the stabilizing structure comprises an annular ridge formed on the upper surface of the upper cover.

12. A filtration assembly as claimed in claim 1 further comprising:
a sample reservoir defining the chamber for holding the fluid sample; and
a base for supporting the sample reservoir, the base being detachably connected to the sample reservoir in a fluid-tight manner without use of a sealing member between the sample reservoir and the base,
one of the sample reservoir and the base having the filter support surface and,
one of the sample reservoir and the base having a projection extending around its periphery and the other sample reservoir and the base having a groove extending around its periphery and detachably engaging the projection in a fluid-tight manner around its periphery.

13. A filtration assembly as claimed in claim 12 wherein the groove and the projection have complementary shapes.

14. A filtration assembly as claimed in claim 12 wherein the groove and the projection are in surface contact around their peripheries.

15. A filtration assembly as claimed in claim 12 wherein the sample reservoir includes a groove and a projection extending around its periphery, and the base includes a groove and a projection extending around its periphery, the projection of the base and the groove in the sample reservoir engaging each other in a fluid-tight manner around their peripheries, and the projection of the sample reservoir and the groove in the base engaging each other in a fluid-tight manner around their peripheries.

16. A filtration assembly as claimed in claim 1 flier comprising:
a sample reservoir defining the chamber for holding the fluid sample to be filtered; and
a base for supporting the sample reservoir and including the fluid port and a skirt surrounding the fluid port for contact with a vacuum manifold of a vacuum filtration assembly, one of the sample reservoir and the base including the filter support surface for supporting the filter element.

17. A method of culturing microorganisms comprising:

introducing a fluid sample into a sample reservoir;

passing the fluid sample through a filter element communicating with an interior of the sample reservoir to filter the fluid;

after filtering the fluid, placing the filter element in a petri dish defined by a cover assembly mountable on the sample reservoir and comprising first and second covers; and incubating microorganisms in the petri dish.

18. A method as claimed in claim 17 further comprising:
before introducing the fluid sample into the sample reservoir, disposing the filter element on a filter support surface formed on one of a sample reservoir and a base and
detachably connecting the sample reservoir to the base in a fluid-tight manner without using a sealing member by engagement between a projection formed on one of the sample reservoir and the base and a groove formed in the other of the sample reservoir and the base.

19. A method as claimed in claim 18 including connecting the sample reservoir to the base with an interference fit.

20. A method as claimed in claim 18 including connecting the sample reservoir to the base with a snap fit.

21. A method as claimed in claim 17 wherein passing the fluid sample through a filter element includes:
placing a base of a filtration assembly on a vacuum manifold with a skirt of the base contacting an inlet tube of the-manifold around a periphery of the skirt and applying suction to an interior of the inlet tube to draw the fluid through the filter element within the filtration assembly and into the manifold.

* * * * *